(12) United States Patent
Kato et al.

(10) Patent No.: US 10,866,211 B2
(45) Date of Patent: Dec. 15, 2020

(54) SEMICONDUCTOR DEVICE AND CELL POTENTIAL MEASURING APPARATUS

(71) Applicant: SONY CORPORATION, Tokyo (JP)

(72) Inventors: Yuri Kato, Kanagawa (JP); Yusuke Oike, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 161 days.

(21) Appl. No.: 16/307,214

(22) PCT Filed: Jun. 7, 2017

(86) PCT No.: PCT/JP2017/021193
§ 371 (c)(1),
(2) Date: Dec. 5, 2018

(87) PCT Pub. No.: WO2017/221714
PCT Pub. Date: Dec. 28, 2017

(65) Prior Publication Data
US 2019/0293597 A1    Sep. 26, 2019

(30) Foreign Application Priority Data

Jun. 21, 2016 (JP) .................................. 2016-122563

(51) Int. Cl.
*G01N 27/416* (2006.01)
*G01N 27/327* (2006.01)
(Continued)

(52) U.S. Cl.
CPC ........... *G01N 27/4161* (2013.01); *C12M 1/34* (2013.01); *C12M 1/42* (2013.01); *G01N 27/00* (2013.01);
(Continued)

(58) Field of Classification Search
CPC ............. G01N 27/3273; G01N 27/403; G01N 27/4148; G01N 27/416
See application file for complete search history.

(56) References Cited

U.S. PATENT DOCUMENTS

| 9,071,209 B1* | 6/2015 | Harrison .......... G01N 33/48728 |
| 2007/0084722 A1* | 4/2007 | Sagawa ................ G01N 2/4168 |
| | | 204/403.01 |

(Continued)

FOREIGN PATENT DOCUMENTS

| AT | 399993 T | 7/2008 |
| CN | 102549417 A | 7/2012 |

(Continued)

OTHER PUBLICATIONS

Zhang et al., "Design of Ultra-Low Power Biopotential Amplifiers for Biosignal Acquisition Applications," IEEE Transactions on Biomedical Circuits and Systems, vol. 6, No. 4, Aug. 2012 (Year: 2012).*

(Continued)

*Primary Examiner* — Alexander S Noguerola
(74) *Attorney, Agent, or Firm* — Chip Law Group (57) ABSTRACT

The present disclosure relates to a semiconductor device and a cell potential measuring apparatus capable of amplifying and reading a potential of solution with high accuracy. A reading electrode reads the potential of the solution. A differential amplifier includes a current mirror circuit. The reading electrode is connected to a first input terminal of the differential amplifier which is connected to a gate of a first input transistor connected to a diode-connected pMOS transistor of the current mirror circuit. An output terminal of the differential amplifier is connected to a second input terminal of the differential amplifier, which is connected to a gate of a second input transistor connected to a pMOS transistor of the current mirror circuit which is not diode-connected, via (Continued)

a capacitor. For example, the present disclosure is applied to the cell potential measuring apparatus and the like.

7 Claims, 7 Drawing Sheets (51) Int. Cl.
*G01N 33/487* (2006.01)
*H03F 3/45* (2006.01)
*C12M 1/34* (2006.01)
*G01N 27/00* (2006.01)
*C12M 1/42* (2006.01)
*G01N 27/414* (2006.01)

(52) U.S. Cl.
CPC ..... *G01N 27/416* (2013.01); *G01N 33/48728* (2013.01); *G01N 33/48735* (2013.01); *H03F 3/45188* (2013.01); *G01N 27/3273* (2013.01); *G01N 27/4148* (2013.01); *H03F 2200/129* (2013.01); *H03F 2200/156* (2013.01); *H03F 2200/228* (2013.01); *H03F 2200/396* (2013.01); *H03F 2200/48* (2013.01); *H03F 2203/45156* (2013.01); *H03F 2203/45512* (2013.01); *H03F 2203/45536* (2013.01)

(56) References Cited

U.S. PATENT DOCUMENTS

| | | |
|---|---|---|
| 2011/0297539 A1 | 12/2011 | Sagawa et al. |
| 2012/0252055 A1 | 10/2012 | Frey et al. |
| 2016/0256068 A1* | 9/2016 | Harrison ............... A61B 5/0428 |

FOREIGN PATENT DOCUMENTS

| | | |
|---|---|---|
| DE | 102009043527 A1 | 4/2011 |
| EP | 1278064 A1 | 1/2003 |
| EP | 2483673 A1 | 8/2012 |
| JP | 03-72368 U | 7/1991 |
| JP | 2002-031617 A1 | 1/2002 |
| JP | 2012-093244 A | 5/2012 |
| JP | 2015-052609 A | 3/2015 |
| JP | 2015-206604 A | 11/2015 |
| WO | 2005/080956 A1 | 9/2005 |
| WO | 2011/039242 A1 | 4/2011 |

OTHER PUBLICATIONS

Theodore Pavlic, "Transistor Basics—Lab 1: The Bipolar (Junction) Transistor," copyright 2007-2009, downloaded on Aug. 6, 2020 from http://www.tedpavlic.com/teaching/osu/ece327/lab1_bjt/lab1_bjt_transistor_basics.pdf (Year: 2009).*

Jafari et al., "Chopper-Stabilized Bidirectional Current Acquisition Circuits for Electrochemical Amperometric Biosensors," IEEE Transactions on Circuits and Systems—I: Regular Papers, vol. 60. 60. No. 5, May 2013 (Year: 2013).*

JPO computer-generated English langauge translation of JP 2014-085316, filed Apr. 17, 2014 (Year: 2015).*

English langauge trasnlation of the Written Opinion for International application No. PCT/JP2017/021193, Dec. 25, 2018 (Year: 2018).*

International Search Report and Written Opinion of PCT Application No. PCT/JP2017/021193, dated Aug. 22, 2017, 02 pages of translation and 07 pages of ISRWO.

* cited by examiner

SEMICONDUCTOR DEVICE AND CELL POTENTIAL MEASURING APPARATUS

CROSS REFERENCE TO RELATED APPLICATIONS

This application is a U.S. National Phase of International Patent Application No. PCT/JP2017/021193 filed on Jun. 7, 2017, which claims priority benefit of Japanese Patent Application No. JP 2016-122563 filed in the Japan Patent Office on Jun. 21, 2016. Each of the above-referenced applications is hereby incorporated herein by reference in its entirety.

TECHNICAL FIELD

The present disclosure relates to a semiconductor device and a cell potential measuring apparatus, and particularly, to a semiconductor device and a cell potential measuring apparatus capable of amplifying and reading a potential of solution with high accuracy.

BACKGROUND ART

There is a device which measures an action potential emitted from living cells by arranging microelectrodes in an array in culture solution including the living cells and electrochemically measuring a potential of the culture solution (for example, refer to Patent Document 1).

In such a device, in recent years, it is devised that a large number of electrodes, amplifiers, analog/digital (A/D) converters, and the like are integrated into a single chip to concurrently measure potentials of a plurality of points by using a Complementary Metal-Oxide Semiconductor (CMOS) integrated circuit technology.

The method of concurrently measuring the potentials at the plurality of points includes a method of measuring the potentials by sequentially connecting the reading electrodes to a single amplifier and a method of measuring the potentials by connecting the reading electrodes to the amplifiers as many as the reading electrodes.

In the former method, since the number of amplifiers is one, noise can be reduced by increasing the size of the amplifier. However, the number of concurrently-measurable points (hereinafter, referred to as the number of concurrently-measured points) is one.

On the other hand, in the latter method, the measurement can be concurrently performed at the plurality of points by concurrently operating the plurality of amplifiers. However, since it is necessary to prepare the amplifiers as many as the reading electrodes, the size of each amplifier is reduced, and the noise increases. As described above, with the above-described method, the noise and the number of concurrently-measured points are in a trade-off state.

Therefore, the latter method is designed to provide an open-loop-type differential amplifier which amplifies and outputs a potential difference between a reference electrode arranged away from a potential generating point in the solution and the reading electrode arranged near the potential generating point instead of the amplifier. In this case, in circuits subsequent to the differential amplifier, noise is suppressed to a reciprocal multiple of an amplification gain of the differential amplifier. Therefore, an increase in the noise caused by the small size of the differential amplifier can be prevented. Therefore, it is possible to increase the number of concurrently-measured points and to prevent the noise.

CITATION LIST

Patent Document

Patent Document 1: Japanese Patent Application Laid-Open No. 2002-31617

SUMMARY OF THE INVENTION

Problems to be Solved by the Invention

However, in the open-loop-type differential amplifier, the output signal is not fed back as an input signal. Therefore, the amplification gain increases, and a range of the input signal to be operated (signal input range) is narrowed. Therefore, it is difficult to amplify and read the potential of the solution with high accuracy.

The present disclosure has been made in view of such circumstances and is intended to amplify and read a potential of solution with high accuracy.

Solutions to Problems

A semiconductor device according to a first aspect of the present disclosure includes a reading electrode that reads a potential of solution and a differential amplifier including a current mirror circuit, in which the reading electrode is connected to a first input terminal of the differential amplifier which is connected to a gate of a first input transistor connected to a diode-connected transistor of the current mirror circuit, and an output terminal of the differential amplifier is connected via a capacitor to a second input terminal of the differential amplifier which is connected to a gate of a second input transistor connected to a transistor of the current mirror circuit which is not diode-connected.

In the first aspect of the present disclosure, a reading electrode that reads a potential of solution and a differential amplifier including a current mirror circuit are included, in which the reading electrode is connected to a first input terminal of the differential amplifier which is connected to a gate of a first input transistor connected to a diode-connected transistor of the current mirror circuit, and an output terminal of the differential amplifier is connected via a capacitor to a second input terminal of the differential amplifier which is connected to a gate of a second input transistor connected to a transistor of the current mirror circuit which is not diode-connected.

A cell potential measuring apparatus according to a second aspect of the present disclosure includes a reading electrode that reads an action potential of a cell included in solution and a differential amplifier including a current mirror circuit, in which the reading electrode is connected to a first input terminal of the differential amplifier which is connected to a gate of a first input transistor connected to a diode-connected transistor of the current mirror circuit, and an output terminal of the differential amplifier is connected via a capacitor to a second input terminal of the differential amplifier which is connected to a gate of a second input transistor connected to a transistor of the current mirror circuit which is not diode-connected.

In the second aspect of the present disclosure, a reading electrode that reads an action potential of cells included in solution and a differential amplifier including a current mirror circuit are included, in which the reading electrode is connected to a first input terminal of the differential amplifier which is connected to a gate of a first input transistor connected to a diode-connected transistor of the current mirror circuit, and an output terminal of the differential amplifier is connected to a second input terminal of the differential amplifier which is connected via a capacitor to a gate of a second input transistor connected to a transistor of the current mirror circuit which is not diode-connected.

Effects of the Invention

According to the first and second aspects of the present disclosure, a potential of solution can be amplified and read with high accuracy.

Note that the effects described herein are not necessarily limited and that the effect may be any effects described in the present disclosure.

MODE FOR CARRYING OUT THE INVENTION

Embodiments for carrying out the present disclosure (referred to as embodiment below) will be described below. Note that, the description will be made in the following order.

1. First embodiment: cell potential measuring apparatus (FIGS. 1 to 4)
2. Second embodiment: cell potential measuring apparatus (FIGS. 5 and 6)
3. Third embodiment: cell potential measuring apparatus (FIG. 7)

First Embodiment (Exemplary Configuration of First Embodiment of Cell Potential Measuring Apparatus)

Figure 1:
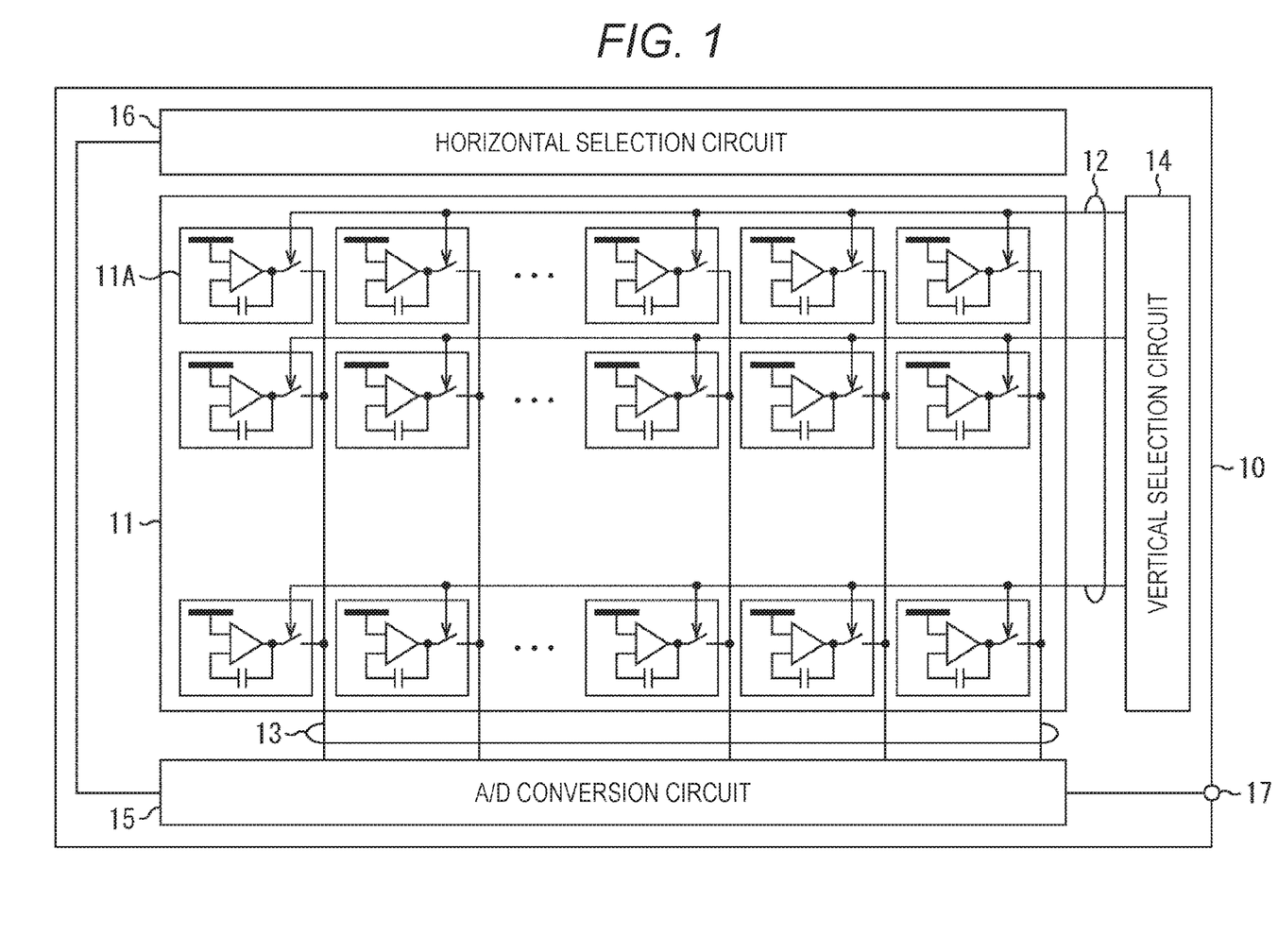
FIG. 1 is a diagram of an exemplary configuration of a first embodiment of a cell potential measuring apparatus to which the present disclosure is applied.

FIG. 1 is a diagram of an exemplary configuration of a first embodiment of a cell potential measuring apparatus to which the present disclosure is applied.

A cell potential measuring apparatus 10 in FIG. 1 is a semiconductor device in which a sensing unit 11, a sensor drive line 12, a vertical signal line 13, a vertical selection circuit 14, an A/D conversion circuit 15, a horizontal selection circuit 16, an output terminal 17 are formed on a semiconductor substrate (chip) which is not shown by using the CMOS integration technology.

In the sensing unit 11 of the cell potential measuring apparatus 10, sensors 11A for reading electrochemical potential of culture solution including living cells are two-dimensionally arranged in an array (matrix). Furthermore, in the sensing unit 11, the sensor drive line 12 is formed for each row of the sensors 11A arranged in an array, and the vertical signal line 13 is formed for each column.

The vertical selection circuit 14 drives the sensors 11A of the sensing unit 11 in units of rows, for example. Specifically, an output end (which is not shown) of the vertical selection circuit 14 corresponding to each row is connected to one end of the sensor drive line 12. The vertical selection circuit 14 sequentially selects each row so as to sequentially read sensor signals from the sensors 11A row by row and outputs a selection signal and the like from the output end connected to the sensor drive line 12 of the selected row. With this operation, the sensor 11A of the selected row reads an electric signal of the potential of the culture solution as a sensor signal and supplies the read signal to the vertical signal line 13.

The A/D conversion circuit 15 includes a signal processing circuit for each column of the sensing unit 11. Each signal processing circuit of the A/D conversion circuit 15 performs signal processing such as A/D conversion processing on the sensor signal output from each sensor of the selected row through the vertical signal line 13. The A/D conversion circuit 15 outputs the signal-processed sensor signal obtained by the selected signal processing circuit via the output terminal 17 according to selection scanning by the horizontal selection circuit 16.

The horizontal selection circuit 16 sequentially selects the signal processing circuits of the A/D conversion circuit 15. By the selection scanning by the horizontal selection circuit 16, the sensor signals on which the signal processing has been performed by the signal processing circuits of the A/D conversion circuit 15 are sequentially output to the output terminal 17.

(Exemplary Configuration of Sensor)

Figure 2:
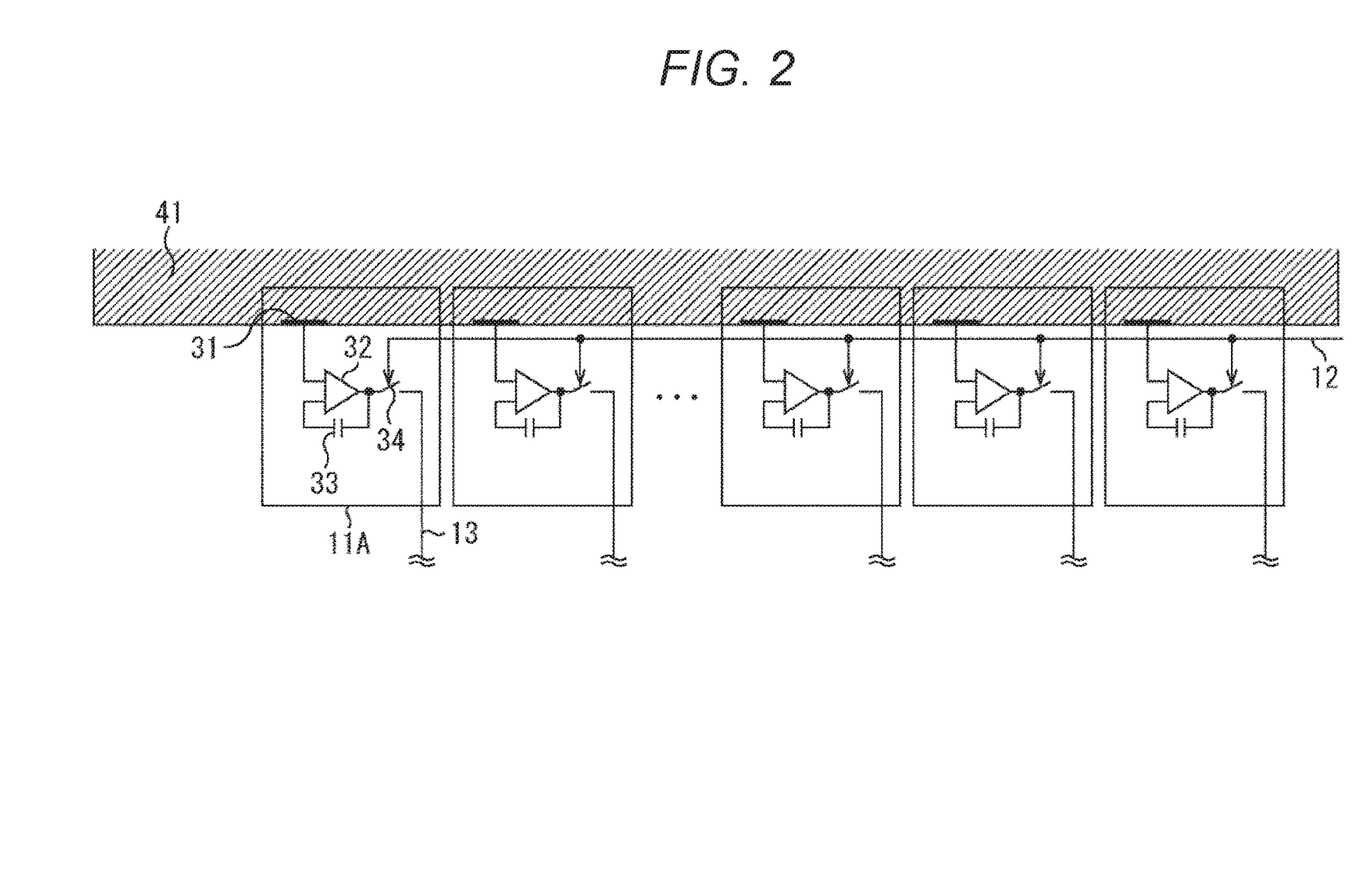
FIG. 2 is a diagram of an exemplary configuration of a sensor in FIG. 1.

FIG. 2 is a diagram of an exemplary configuration of the sensor 11A in FIG. 1.

In FIG. 2, for convenience of description, only the sensors 11A in a single row are illustrated.

As illustrated in FIG. 2, the sensor 11A includes a reading electrode 31, a differential amplifier 32, a capacitor 33, and a switch 34.

The reading electrode 31 of the sensor 11A in FIG. 2 is arranged in culture solution 41 including living cells. The reading electrode 31 reads an electric signal of a potential of the culture solution 41 as an electric signal of an action potential of the living cell included in the culture solution 41.

The differential amplifier 32 receives the electric signal read by the reading electrode 31 as an input signal and receives an output signal output from the differential amplifier 32 via the capacitor 33 as an input signal. The differential amplifier 32 amplifies a potential difference between the two input signals and outputs the amplified difference as an output signal. The output signal is input to the capacitor 33 and the switch 34.

The switch 34 outputs the output signal to the vertical signal line 13 as a sensor signal on the basis of the selection signal input by the sensor drive line 12 in FIG. 1. Specifically, in a case where the selection signal has been input, that is, in a case where a row of the sensor 11A is the selected row, the switch 34 outputs the output signal to the vertical signal line 13 as a sensor signal. On the other hand, in a case where the selection signal is not input, that is, in a case where the row of the sensor 11A is not the selected row, the switch 34 does not output the output signal to the vertical signal line 13 as a sensor signal.

(Example of Detailed Configuration of Differential Amplifier)

Figure 3:
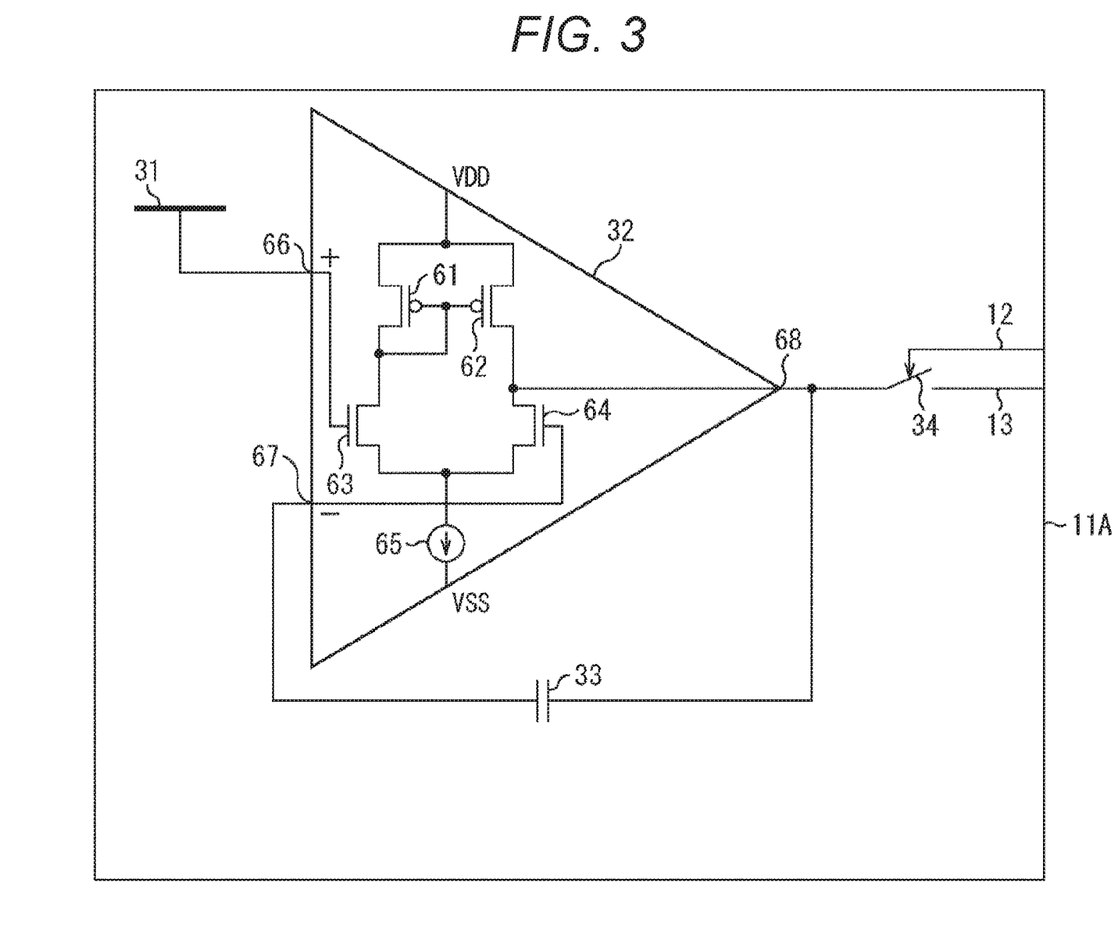
FIG. 3 is a diagram of an example of a detailed configuration of a differential amplifier in FIG. 2.

FIG. 3 is a diagram of an example of a detailed configuration of the differential amplifier 32 in FIG. 2.

The differential amplifier 32 in FIG. 3 includes a current mirror circuit including pMOS transistors 61 and 62 which are diode-connected to each other as a load resistor. Specifically, the differential amplifier 32 includes the pMOS transistors 61 and 62, input transistors 63 and 64 include nMOS transistors, a constant current source 65, input terminals 66 and 67, and an output terminal 68.

The pMOS transistor 61 is connected to the input transistor 63 in series, and the pMOS transistor 62 is connected to the input transistor 64 in series. Furthermore, the pMOS transistors 61 and 62 are connected to a power supply potential VDD, and the input transistors 63 and 64 are connected to an earth potential VSS via the constant current source 65.

In the input transistors 63 and 64, a gate of the input transistor 63 which is connected to the diode-connected pMOS transistor 61 and to which an amplification gain is not applied is connected to the input terminal 66 connected to the reading electrode 31. Furthermore, a gate of the input transistor 64 which is connected to the pMOS transistor 62 which is not diode-connected and to which the amplification gain is applied is connected to the input terminal 67 connected to the output terminal 68 via the capacitor 33. With this connection, a closed loop for feeding back the output signal of the differential amplifier 32 as an input signal is formed. Furthermore, the output terminal 68 is connected to a connection point between the pMOS transistor 62 and the input transistor 64.

As described above, the differential amplifier 32 forms the closed loop for feeding back the output signal as an input signal. Therefore, in comparison with an open-loop-type differential amplifier, it is possible to reduce the amplification gain and widen the signal input range.

Furthermore, since no circuit is inserted between the reading electrode 31 and the input transistor 63 in the differential amplifier 32, one or less amplification gain is not applied to the input signal, and Signal/Noise (S/N) does not deteriorate.

Whereas, in a case where any circuit is inserted between the reading electrode 31 and the input transistor 63, one or less amplification gain is applied to the input signal, and the S/N deteriorates. Therefore, to prevent the deterioration in the S/N, it is necessary to arrange a large capacitor near the reading electrode 31. Therefore, it is difficult to reduce a pitch between the reading electrodes 31 and increase the number of sensors 11A, that is, the number of concurrently-measured points.

Furthermore, since the output signal is not fed back to the reading electrode 31 in the differential amplifier 32, it can be prevented that a fluctuation of the potential of the reading electrode 31 caused by the feedback of the output signal affects an activity of the living cell and an accurate action potential cannot be measured.

Note that, in the differential amplifier 32, by a parasitic capacitor between the gate and a drain of the input transistor 63, there is a possibility that the output signal is fed back to the reading electrode 31. However, since the amplification gain is not applied to the input transistor 63, the fluctuation of the potential of the reading electrode 31 caused by the feedback is small.

(Description of Signal Input Range)

Figure 4:
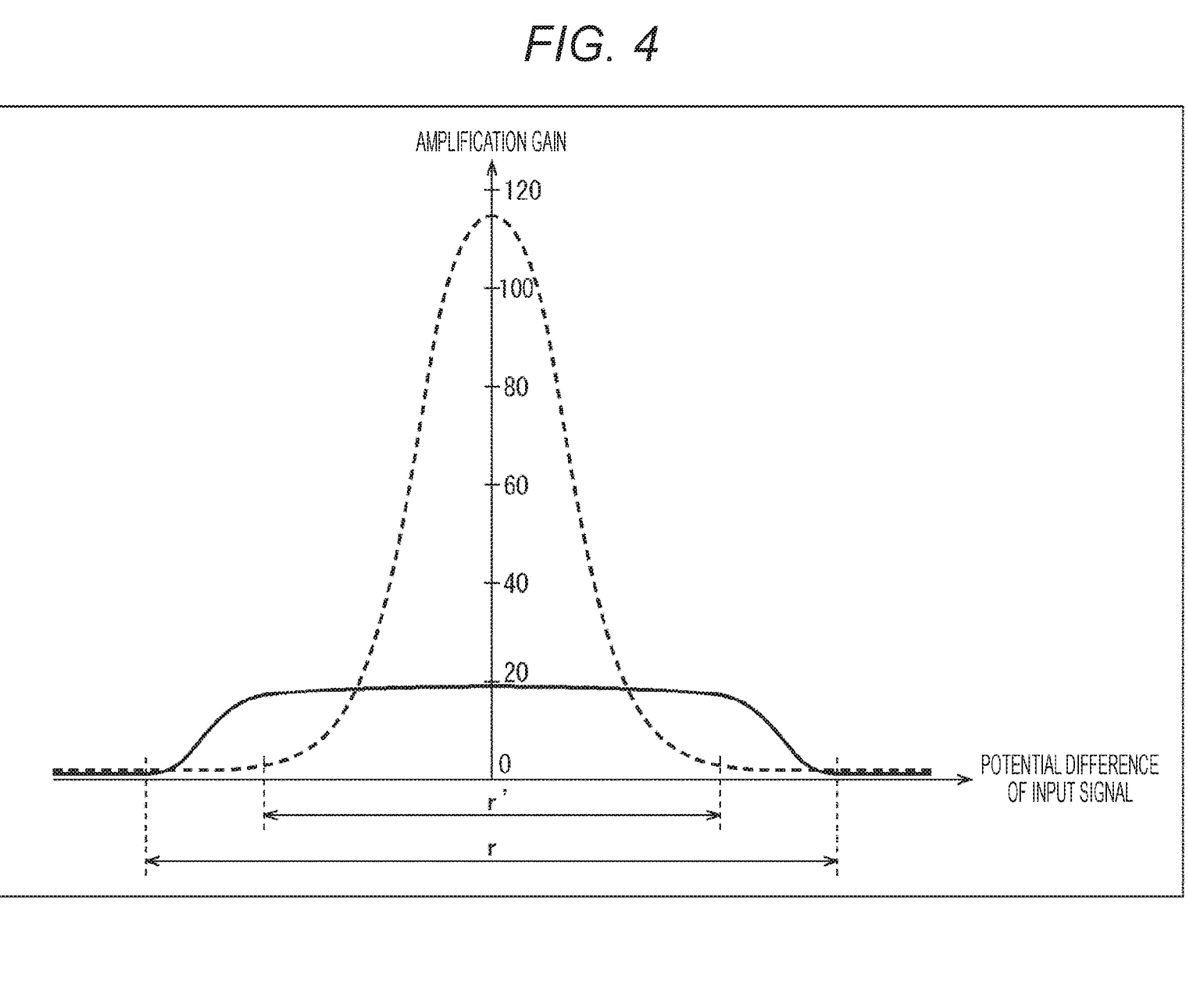
FIG. 4 is a diagram for explaining a signal input range of the differential amplifier in FIG. 3.

FIG. 4 is a diagram for explaining the signal input range of the differential amplifier 32 in FIG. 3.

In a graph in FIG. 4, the horizontal axis indicates a potential difference between a potential Vin(+) of the input signal input to the input terminal 66 and a potential Vout(−) of the input signal input to the input terminal 67, and the vertical axis indicates an amplification gain of the differential amplifier. Furthermore, a solid line indicates the amplification gain of the differential amplifier 32 with respect to each potential difference, and a dotted line indicates an amplification gain of the open-loop-type differential amplifier with respect to each potential difference.

As indicated by the dotted line in FIG. 4, regarding the open-loop-type differential amplifier, the amplification gain increases, and a signal input range r' is narrowed. On the other hand, since the differential amplifier 32 forms the closed loop, regarding the differential amplifier 32, as indicated by the solid line in FIG. 4, the amplification gain decreases, a signal input range r is wider than the signal input range r'. As a result, the differential amplifier 32 can amplify the potential difference of the input signals with high accuracy. In other words, the electric signal of the potential of the culture solution 41 read by the reading electrode 31 can be amplified with high accuracy.

Second Embodiment (Exemplary Configuration of Second Embodiment of Cell Potential Measuring Apparatus)

Figure 5:
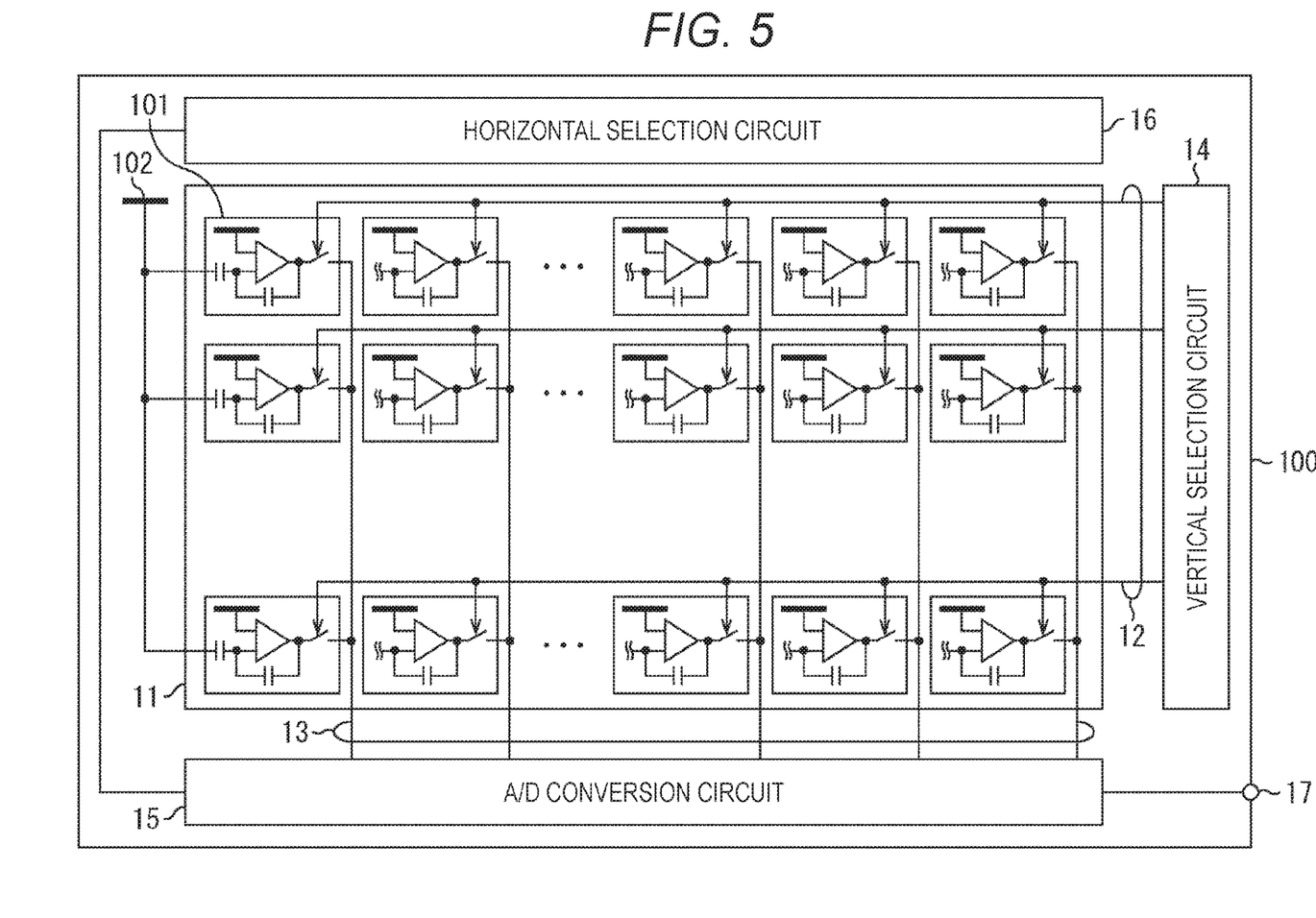
FIG. 5 is a block diagram of an exemplary configuration of a second embodiment of the cell potential measuring apparatus to which the present disclosure is applied.

FIG. 5 is a block diagram of an exemplary configuration of a second embodiment of the cell potential measuring apparatus to which the present disclosure is applied.

The components illustrated in FIG. 5 same as those in the configuration in FIG. 1 are denoted with the same reference numerals. The overlapped description will be appropriately omitted.

A configuration of a cell potential measuring apparatus 100 in FIG. 5 is different from the configuration of the cell potential measuring apparatus 10 in FIG. 1 in that sensors 101 are provided instead of the sensors 11A and that a reference electrode 102 is newly provided. In the cell potential measuring apparatus 100, not only the electric signal of the potential of the reading electrode 31 but also an electric signal of a potential of the reference electrode 102 is input to the sensor 101.

Specifically, the sensor 101 of the cell potential measuring apparatus 100 generates a sensor signal by using the electric signal of the potential of the reading electrode 31 and the electric signal of the potential of the reference electrode 102. The reference electrode 102 is arranged away from living cells in culture solution and reads a reference potential of the culture solution. The reference electrode 102 supplies the read electric signal of the reference potential to each sensor 101.

(Example of Detailed Configuration of Differential Amplifier)

Figure 6:
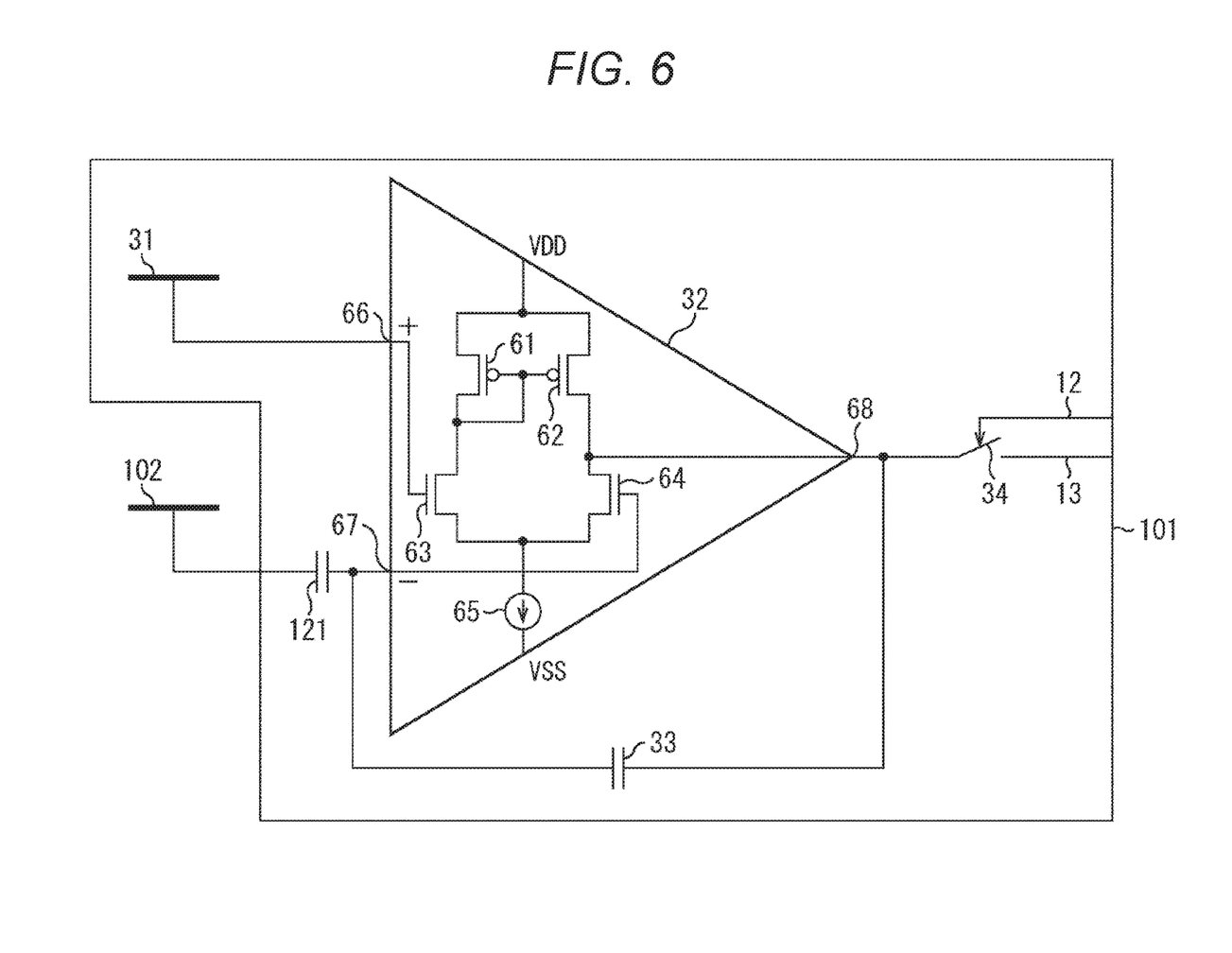
FIG. 6 is a diagram of an example of a detailed configuration of a sensor in FIG. 5.
Figure 7:
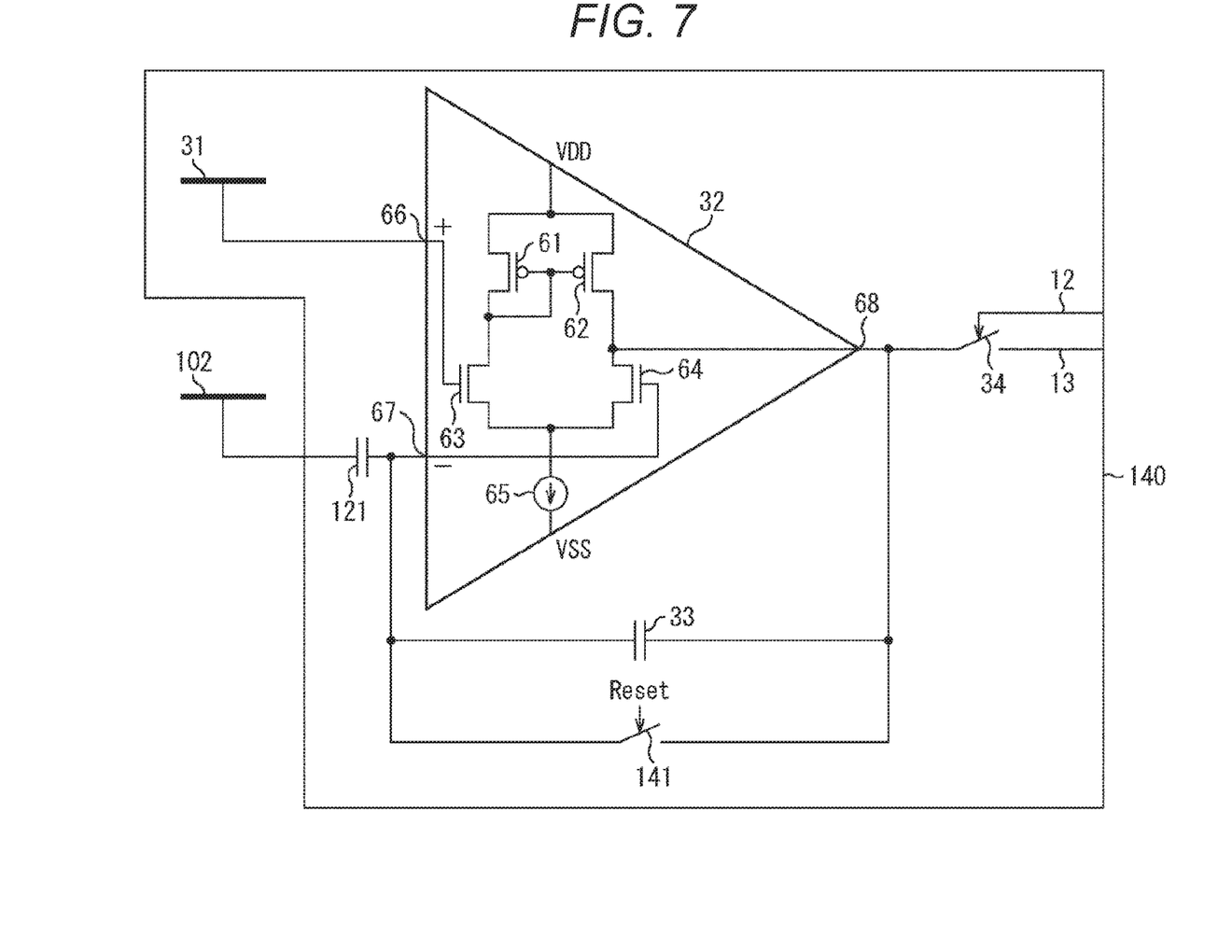
FIG. 7 is a diagram of an exemplary configuration of a sensor according to a third embodiment of the cell potential measuring apparatus to which the present disclosure is applied.

FIG. 6 is a diagram of an example of a detailed configuration of the sensor 101 in FIG. 5.

The components illustrated in FIG. 6 same as those in the configuration in FIG. 3 are denoted with the same reference numerals. The overlapped description will be appropriately omitted.

The configuration of the sensor 101 in FIG. 5 is different from the configuration of the sensor 11A in that the reference electrode 102 is connected to the input terminal 67 via a capacitor 121.

Since the reference electrode 102 is connected to the input terminal 67 via the capacitor 121 in the sensor 101, the differential amplifier 32 can cancel noise components mixed in the reading electrode 31 and the reference electrode 102 in phase. As a result, noise of the output signal output from the differential amplifier 32 can be reduced.

Third Embodiment (Exemplary Configuration of Sensor of Third Embodiment of Cell Potential Measuring Apparatus)

A configuration of a third embodiment of the cell potential measuring apparatus to which the present disclosure is applied is the same as the cell potential measuring apparatus 100 in FIG. 5 except for the configuration of the sensor. Therefore, the configuration of the sensor will be described below.

FIG. 7 is a diagram of an exemplary configuration of a sensor according to the third embodiment of the cell potential measuring apparatus to which the present disclosure is applied.

The components illustrated in FIG. 7 same as those in the configuration in FIG. 6 are denoted with the same reference numerals. The overlapped description will be appropriately omitted.

A configuration of a sensor 140 in FIG. 7 is different from the configuration of the sensor 101 in FIG. 6 in that a reset switch 141 is connected between the output terminal 68 and the input terminal 67 in parallel to the capacitor 33.

The reset switch 141 short-circuits the output terminal 68 and the input terminal 67 on the basis of a reset signal Reset supplied from a control circuit which is not shown. With this operation, currents on the side of the pMOS transistor 61 and the side of the pMOS transistor 62 of the differential amplifier 32 are balanced, and a state where the potential difference of the input signals is zero (Vin(+)−Vin(−)=0) can be sampled and held as an input voltage of the reference electrode 102.

In other words, it is possible to cancel a mismatch of thresholds of the input transistors 63 and 64 and reset an operation point of the differential amplifier 32. Therefore, it can be prevented that offsets different for the respective sensors 140 due to the mismatch of the thresholds of the input transistors 63 and 64 are superimposed on the input signal and the amplification gains relative to the same input signal vary between the sensors 140. As a result, variations in the values of the sensor signals between the sensors 140 can be prevented.

Note that the effects described herein are only exemplary and not limited to these. There may be an additional effect.

Furthermore, the embodiments of the present disclosure are not limited to the embodiments described above and can be variously changed without departing from the scope of the present disclosure.

For example, in the first embodiment, the reset switch 141 may be connected in parallel to the capacitor 33 as in the third embodiment.

Note that the present disclosure can have a configuration below.

(1)
A semiconductor device including:
a reading electrode configured to read a potential of solution; and
a differential amplifier including a current mirror circuit, in which
the reading electrode is connected to a first input terminal of the differential amplifier which is connected to a gate of a first input transistor connected to a diode-connected transistor of the current mirror circuit, and an output terminal of the differential amplifier is connected via a capacitor to a second input terminal of the differential amplifier which is connected to a gate of a second input transistor connected to a transistor of the current mirror circuit which is not diode-connected.

(2)
The semiconductor device according to (1), in which
the second input terminal is connected to a reference electrode for reading a reference potential of the solution.

(3)
The semiconductor device according to (2), in which
the second input terminal is connected to the reference electrode via a capacitor.

(4)
The semiconductor device according to any one of (1) to (3), in which
a switch is connected between the output terminal and the second input terminal in parallel to the capacitor.

(5)
The semiconductor device according to any one of (1) to (4), in which
the output terminal is connected to a connection point between the transistor of the current mirror circuit which is not diode-connected and the second input transistor.

(6)
The semiconductor device according to any one of (1) to (5), in which
the reading electrodes are arranged in an array.

(7)
A cell potential measuring apparatus including:
a reading electrode configured to read an action potential of a cell included in solution; and
a differential amplifier including a current mirror circuit, in which
the reading electrode is connected to a first input terminal of the differential amplifier which is connected to a gate of a first input transistor connected to a diode-connected transistor of the current mirror circuit, and
an output terminal of the differential amplifier is connected via a capacitor to a second input terminal of the differential amplifier which is connected to a gate of a second input transistor connected to a transistor of the current mirror circuit which is not diode-connected.

REFERENCE SIGNS LIST 10 cell potential measuring apparatus
31 reading electrode
32 differential amplifier
33 capacitor
41 culture solution
61, 62 pMOS transistor
63, 64 input transistor
66, 67 input terminal
68 output terminal
100 cell potential measuring apparatus
102 reference electrode
121 capacitor
141 reset switch

The invention claimed is:

1. A semiconductor device, comprising:
a reading electrode configured to read a potential of solution; and
a differential amplifier including a current mirror circuit, wherein
the reading electrode is connected to a first input terminal of the differential amplifier which is connected to a gate of a first input transistor connected to a diode-connected transistor of the current mirror circuit, and an output terminal of the differential amplifier is connected via a first capacitor to a second input terminal of the differential amplifier which is connected to a gate of a second input transistor connected to a transistor of the current mirror circuit which is not diode-connected.

2. The semiconductor device according to claim 1, wherein
the second input terminal is connected to a reference electrode to read a reference potential of the solution.

3. The semiconductor device according to claim 2, wherein
the second input terminal is connected to the reference electrode via a second capacitor.

4. The semiconductor device according to claim 1, wherein
a switch is connected between the output terminal and the second input terminal in parallel to the first capacitor.

5. The semiconductor device according to claim 1, wherein
the output terminal is connected to a connection point between the transistor of the current mirror circuit which is not diode-connected and the second input transistor.

6. The semiconductor device according to claim 1, further comprising a plurality reading electrodes arranged in an array.

7. A cell potential measuring apparatus, comprising:
a reading electrode configured to read an action potential of a cell included in solution; and
a differential amplifier including a current mirror circuit, wherein
the reading electrode is connected to a first input terminal of the differential amplifier which is connected to a gate of a first input transistor connected to a diode-connected transistor of the current mirror circuit, and
an output terminal of the differential amplifier is connected via a capacitor to a second input terminal of the differential amplifier which is connected to a gate of a second input transistor connected to a transistor of the current mirror circuit which is not diode-connected.

* * * * *